United States Patent [19]

Adams et al.

[11] Patent Number: 5,023,250
[45] Date of Patent: Jun. 11, 1991

[54] STEROIDAL 14ALPHA-CARBOXY-ALKYL DERIVATIVES AS REGULATORS OF HMG-COA REDUCTASE

[75] Inventors: Jerry L. Adams, Wayne; Timothy F. Gallagher, Harleysville; Ruth J. Mayer, Wayne; Brian W. Metcalf, Radnor, all of Pa.

[73] Assignee: SmithKline Beecham Corporation, Philadelphia, Pa.

[21] Appl. No.: 398,206

[22] Filed: Aug. 24, 1989

[51] Int. Cl.$^5$ .................... A61K 31/575; E07J 9/00
[52] U.S. Cl. .................... 514/179; 552/540; 552/542; 552/544; 552/547
[58] Field of Search .......... 552/540, 542, 544, 547; 514/179

[56] References Cited

U.S. PATENT DOCUMENTS 4,202,891  5/1980  Schroepfer et al. ................ 424/242

FOREIGN PATENT DOCUMENTS

276823-A2  8/1988  European Pat. Off. .

OTHER PUBLICATIONS

Cooper et al., J. Chem. Soc., Chem, Commun. 898–900 (1989).
Trzaskos et al., J. Biol. Chem., 261, No. 36, 16937–42 (1986).

*Primary Examiner*—Jane T. Fan
*Assistant Examiner*—Celia Chang
*Attorney, Agent, or Firm*—Wayne J. Dustman; Stuart R. Suter; Edward T. Lentz

[57] ABSTRACT

New 14α-carboxyalkyl sterols are regulators of HMG—CoA reductase and inhibitors of mammalian 14α-methyl demethylase and are useful in lowering serum cholesterol levels and treating fungal infections.

12 Claims, No Drawings

STEROIDAL 14ALPHA-CARBOXY-ALKYL DERIVATIVES AS REGULATORS OF HMG-COA REDUCTASE

The present invention relates to certain novel 14α-carboxyalkyl steroid compounds that inhibit mammalian lanosterol 14α-methyl demethylase and effect the activity of 3-hydroxy-3-methylglutaryl coenzyme A reductase, both of which are important enzymes in the biosynthesis of cholesterol. These compounds lower serum cholesterol levels and are useful in the treatment of hypercholesterolemia.

Intermediates useful in preparing the 14α-carboxyalkyl steroids are also objects of this invention.

This invention also relates to pharmaceutical compositions containing the 14α-carboxysteroids and to methods of using these compounds.

BACKGROUND OF THE INVENTION

It is known that elevated levels of serum cholesterol may lead to atherosclerosis and coronary heart disease. Therefore compounds which inhibit the biosynthesis of cholesterol and thereby effect serum cholesterol levels are of interest.

Lanosterol is an intermediate in the biosynthesis of cholesterol, requiring, among other transformations, enzymatic removal of the methyl group at carbon 14. The removal of the methyl group from carbon 14 is effected by the enzyme lanosterol 14α-methyl demethylase. Oxidative removal of the C-14 methyl group by the cytochrome P-450 dependent lanosterol 14α-methyl demethylase produces 30-oxygenated steroids (14-$CH_2OH$ and 14-CHO) as intermediates. These oxygenated intermediates are proposed to play a role as regulatory steroids in the control of the overall biosynthetic pathway of cholesterol. The activity of 3-hydroxy-3-methylglutaryl coenzyme A reductase (HMG-CoA reductase), which is a rate-limiting enzyme in cholesterol biosynthesis, is also proposed to be influenced by changes in the concentration of oxygenated intermediates in the reaction of lanosterol 14α-methyl demethylase. Relevant references are Havel et al, *J. Biol. Chem.*, 254:9573 (1979), Gibbons et al, *J. Biol. Chem.*, 255:395 (1980).

The ability of certain naturally occurring and synthetic oxysterols to suppress the activity of HMG-CoA reductase in whole cells has been demonstrated. Gibbons, *Biochemical Society Transactions*, 11:649 (1983); Parish et al, *Lipids*, 21:26 (1986); Trzaskos et al, *J. Biol. Chem.*, 261:16937 (1986).

Recognition of the importance of reducing cholesterol biosynthesis has stimulated efforts to synthesize inhibitors of lanosterol 14α-methyl demethylase as well as oxysterol regulators of HMG-CoA reductase activity.

European Patent Application 276,823 (Aug. 3, 1988) disclosed the use of 14,15-substituted lanosterol including 14-carboxy sterols, as hypocholesterolemic agents. The substituted lanosterols are described as active in inhibiting lanosterol 14α-methyl demethylase activity and suppressing HMG-CoA activity.

In U.S. Pat. No. 4,202,891, Schroepfer et al disclosed 15-oxygenated sterols as inhibitors of mevalonic acid formation, mevalonic acid being an intermediate in the biosynthesis of cholesterol.

Parish et al, in *Lipids*, 21:27 (1986) "Oxysterols: Chemical Synthesis, Biosynthesis and Biological Activities" report on the inhibition of HMG-CoA reductase activity by 9α,11α-epoxycholest-7-en-3β-ol, 3β-hydroxycholest-8-en-7-one and 3β-hydroxycholest-8-en-11-one. Parish et al also note that 14α-hydroxymethyl derivatives of 24,25-dihydrolanosterol have been reported as potent inhibitors of HMG-CoA reductase activity in whole cells.

Shafiee et al, *J. Lipid Res.*, 27:1, (1986) reported on 14-aldehyde sterols.

Cheng et al, *J. Chem. Soc. Perkin. Trans. I.*, 2403 (1988) reported the isolation of a 14-carboxy sterol (penasterol) from a marine sponge.

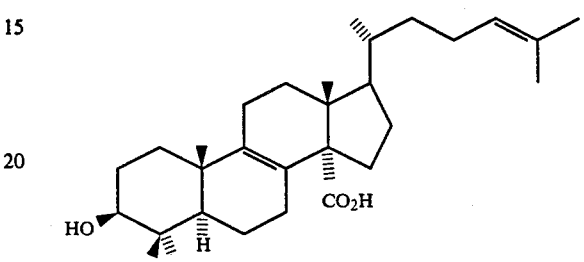

DESCRIPTION OF THE INVENTION

The present invention resides in the discovery that lanosterol 14α-methyl demethylase is inhibited and 3-hydroxy-3-methylglutaryl-coenzyme A reductase activity is suppressed and thus, cholesterol biosynthesis is regulated by certain 14α-carboxyalkyl derivatives of steroidal compounds. The compounds are potent inhibitors of both lanosterol 14α-methyl demethylase and 3-hydroxy-3-methyl-glutaryl reductase activity.

The compounds also have antifungal activity, for example, activity against *Candida albicans*.

The compounds of this invention that inhibit cholesterol biosynthesis are represented by the following Formula I:

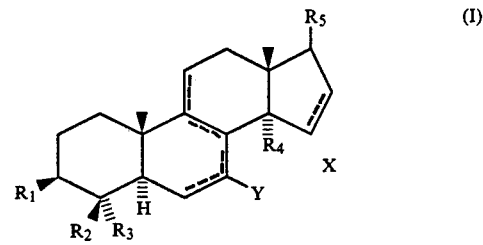

in which:

the B, C, and D rings have optional double bonds where indicated by the dotted lines, provided that the B and C rings do not have adjacent double bonds;

X and Y are H, F, OH, $OR_6$, $OCOR_7$ or keto; said X and Y being H or F when adjacent to a double bond;

$R_1$ is OH, $OR_6$, $OCOR_7$ or keto;

$R_2$ and $R_3$ are H, $C_1$-$C_4$alkyl or F;

$R_4$ is $(CH_2)_nCOOR_7$; $CHFCOOR_7$ or CHOH-$COOR_7$;

$R_5$ is

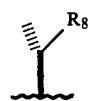

$R_6$ is $C_1$-$C_4$alkyl or benzyl;

$R_7$ is H, $C_1$-$C_6$alkyl or phenyl;

$R_8$ is $C_1$-$C_{11}$alkyl optionally substituted by hydroxy or carbonyl; or $C_2$-$C_{11}$alkenyl; and n is 1 or 3.

Particular compounds of Formula I are those in which $R_5$ is $C_8H_{17}$ or $C_8H_{15}$, particularly the following:

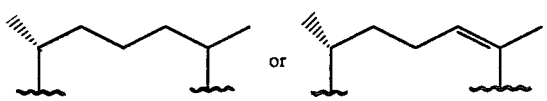

also, particular $R_5$ groups are the following:

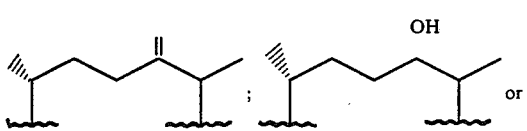

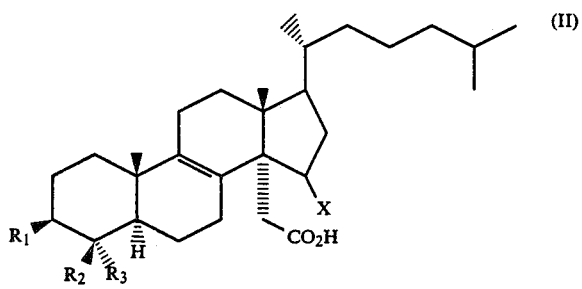

Preferred among the compounds of this invention are those having Formula II:

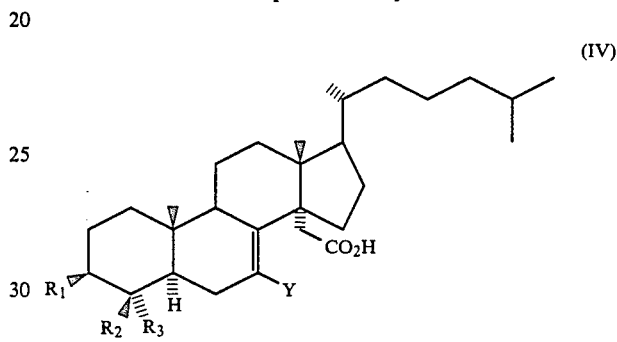

(II)

in which:

$R_2$ and $R_3$ are H or $CH_3$;

X is H or keto and $R_1$ is as defined in Formula I.

Also preferred among the compounds of this invention are those that have Formula III:

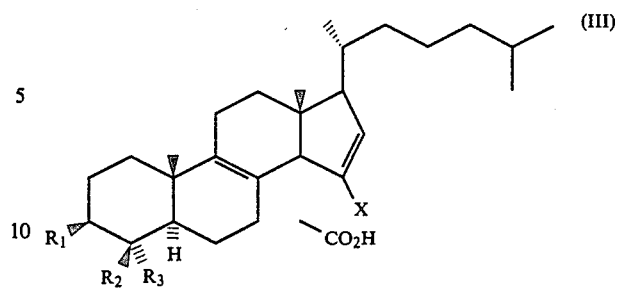

(III)

in which:

$R_2$ and $R_3$ are H or $CH_3$;

X is H or F and $R_1$ is as defined in Formula I.

Also preferred among the compounds of the present invention are those represented by Formula IV:

(IV)

in which:

$R_2$ and $R_3$ are H or $CH_3$;

Y is H or F; and $R_1$ is as defined in Formula I.

Particular compounds of this invention and particular compounds used in the pharmaceutical compositions and methods of this invention include:

3β-hydroxy-lanost-8,15-dien-30-carboxylic acid,
3β-hydroxy-15-oxo-lanost-8-en-30-carboxylic acid,
3β-hydroxy-14α-carboxymethyl-5α-cholest-8,15-diene,
3β-hydroxy-14α-carboxymethyl-15-oxo-5α-cholest-8-ene,
3β-hydroxy-lanost-8-en-30-carboxylic acid,
3β-hydroxy-14α-carboxymethyl-5α-cholest-8-ene,
3β-benzoyloxy-lanost-8-en-30-carboxylic acid,
3β-methoxy-lanost-8-en-30-carboxylic acid,
3β-hydroxy-15-oxo-lanost-8-en-30-acetic acid,
3β-hydroxy-lanost-8,15-dien-30-acetic acid,
3β-hydroxy-lanost-8-en-30-acetic acid,
3β-hydroxy-lanost-7-en-30-carboxylic acid,
3β-hydroxy-lanostan-30-carboxylic acid,
3β-hydroxy-14α-carboxymethyl-5α-cholest-7-ene,
3β-hydroxy-14α-carboxymethyl-5α-cholestane,
3β-hydroxy-lanost-6-en-30-carboxylic acid,
3β-hydroxy-lanost-8-en-30-carboxylic acid ethyl ester,
3-oxo-lanost-8,15-dien-30-carboxylic acid.

A further aspect of the invention relates to novel intermediates useful in preparing the presently invented HMG-CoA reductase regulating and lanosterol 14α-methyl demethylase inhibiting compounds.

Also included in this invention are pharmaceutically acceptable salts of the compounds of Formula I. Pharmaceutically acceptable base addition salts of compounds of the invention containing an acidic group are prepared by known methods from organic and inorganic bases including nontoxic alkali metal and alkaline earth bases, for example, calcium, sodium, and potassium hydroxide; ammonium hydroxide, and nontoxic organic bases such as triethylamine, butylamine, piperazine, and (trihydroxymethyl)methylamine. Also esters of the 3-hydroxy compounds such as the hemisuccinate from succinic acid and the sulfate from sulfuric acid. The sulfates and hemisuccinates are useful to improve absorption and solubility and thus to improve drug deliveries.

As used above and through the remainder of the specification and claims the carbons of the steroid nucleus are numbered are numbered and the rings are lettered as follows:

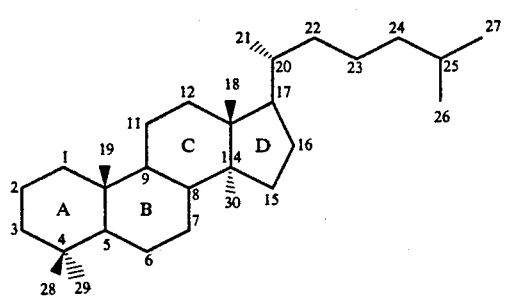

The compounds of this invention are prepared by procedures described herebelow and illustrated by the examples. Reagents, protecting groups and functionality on the steroid and other fragments of the molecule must be consistent with the proposed chemical transformations. Steps in the synthesis must be compatible with the functional groups and the protecting groups.

Formula I compounds are prepared as described in Schemes I through V where the R terms and X, Y and n are as defined in Formulas I through IV.

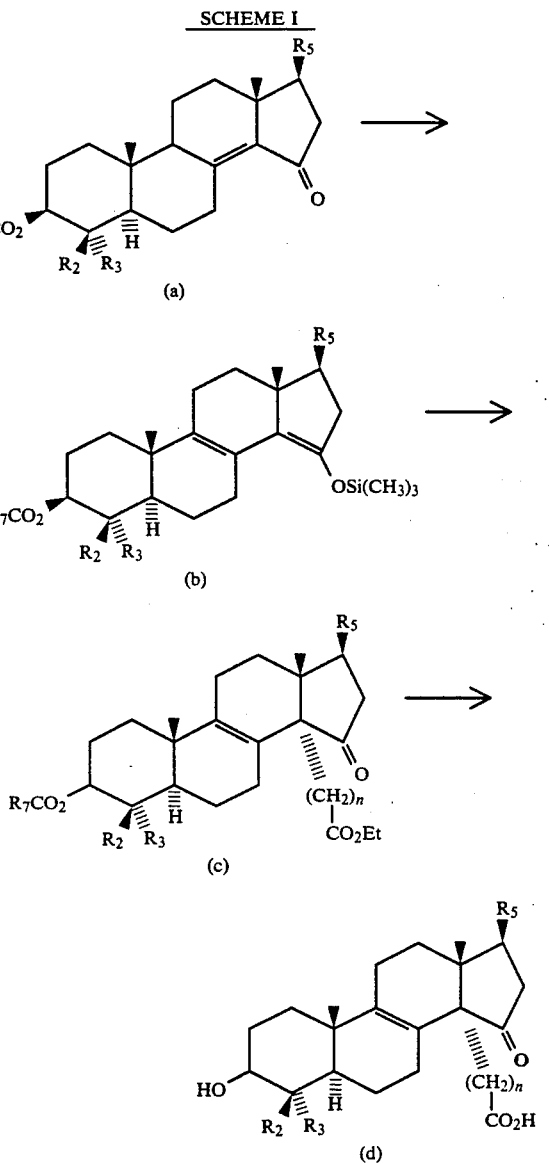

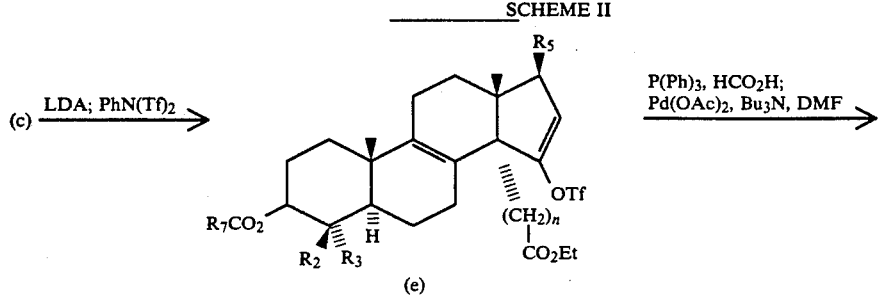

-continued
SCHEME II
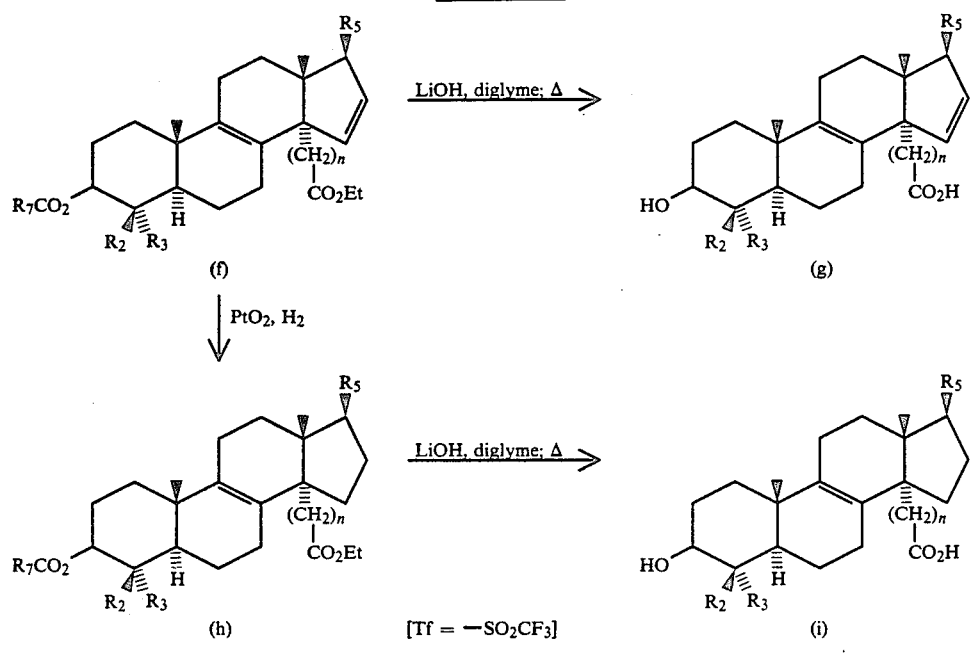
SCHEME III
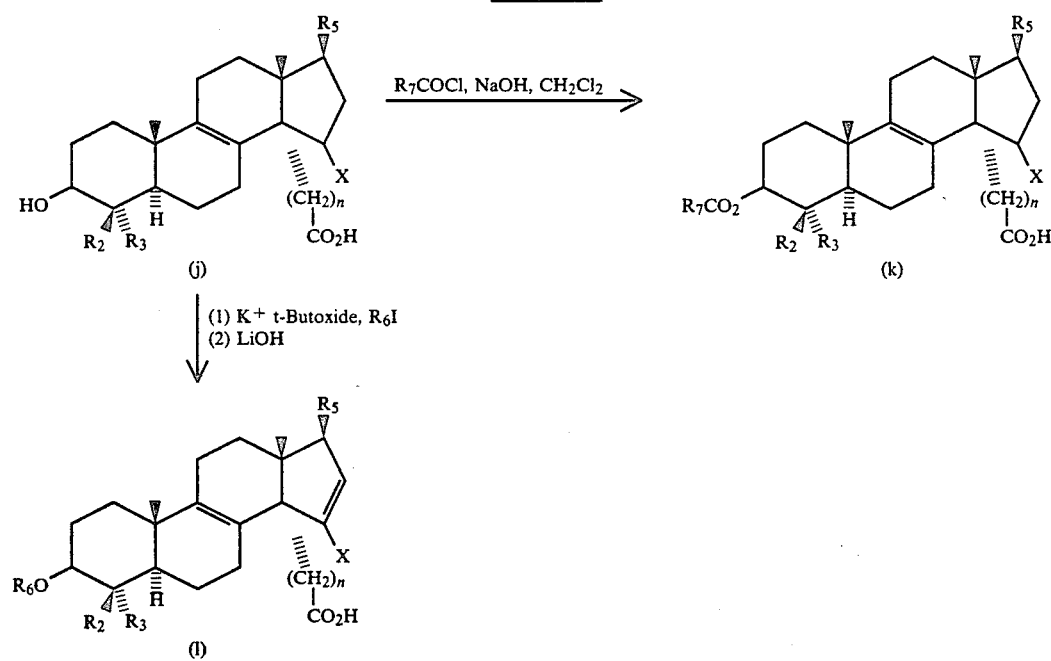
Scheme IV
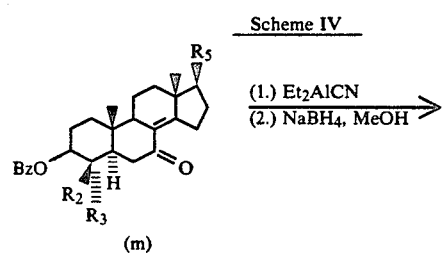
-continued
Scheme IV
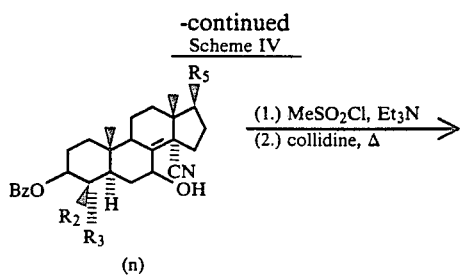

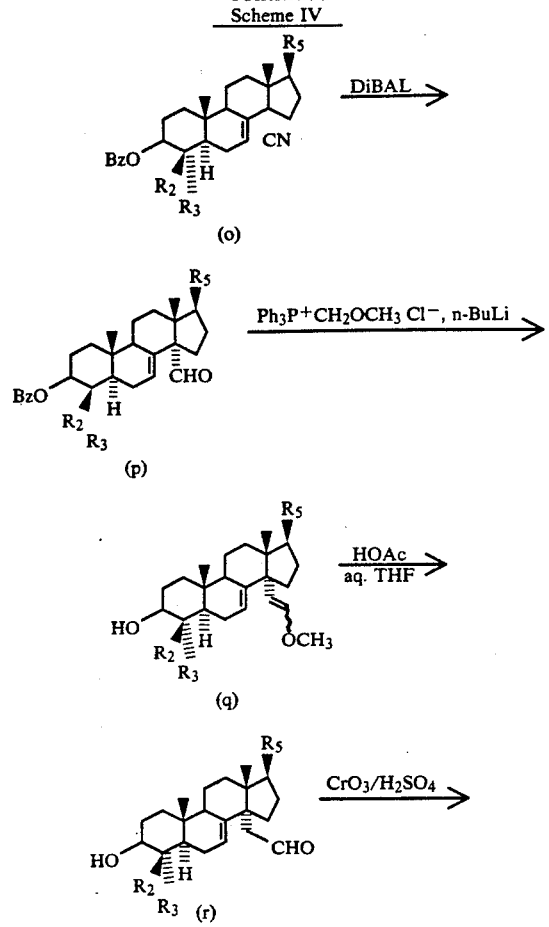
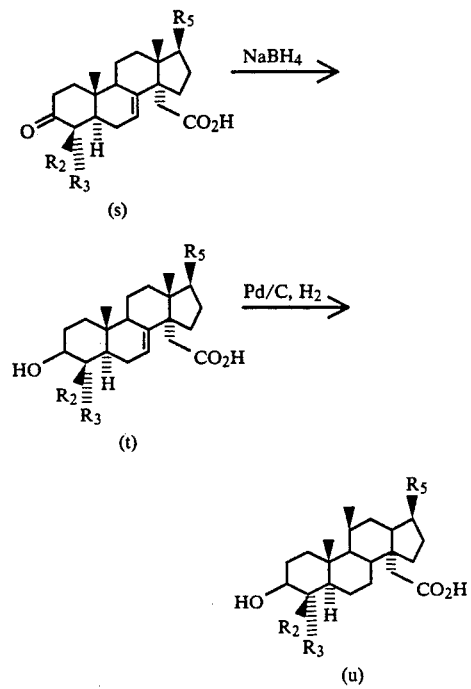
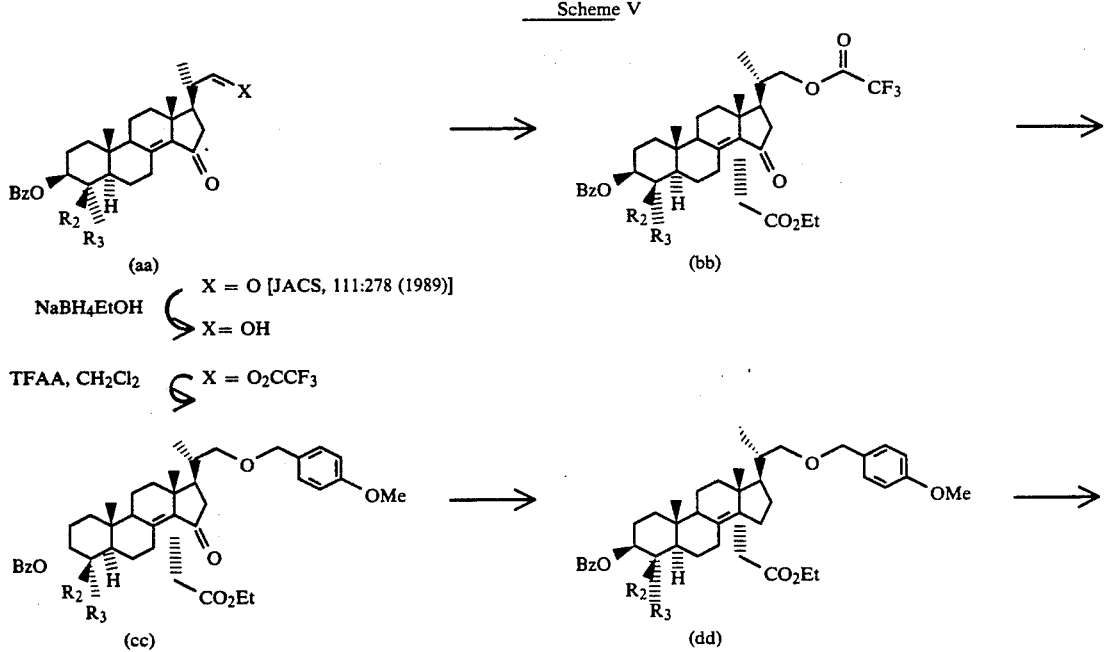

-continued
Scheme V

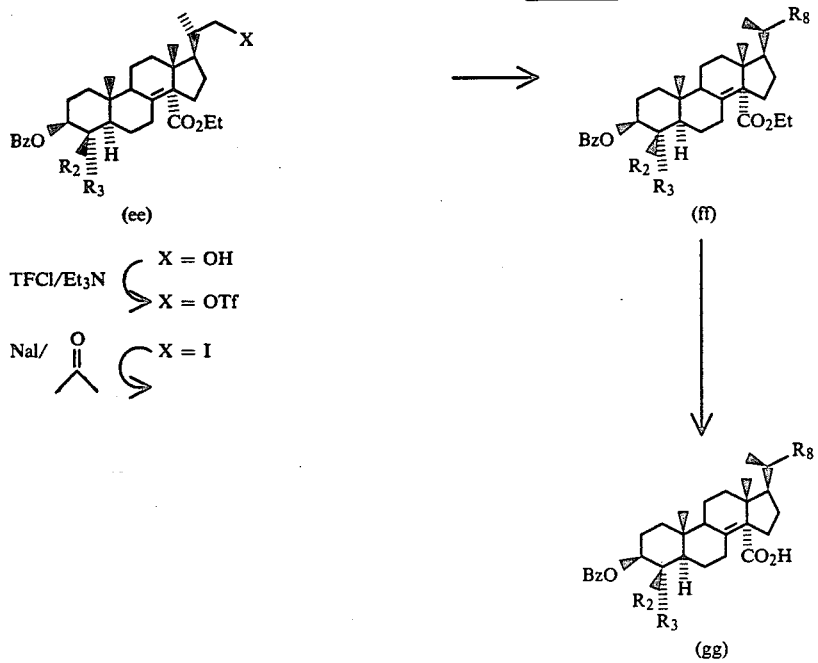

Scheme I depicts formation of Formula I compounds having a double bond at $C_8-C_9$; X is O and Y is H. The starting $C_8-C_{14}$-ene-15-one compounds of formula (a) are known [(J. Biol. Chem., 241:1502; (1966) Chem. Phys. Lipids, 47:187 (1988); J. Org. Chem., 51:4047 (1986)] and are readily available or are synthesized from available precursors using known procedures. According to Scheme I, a solution of a $C_8-C_{14}$-ene-15-one compound (a) in an appropriate organic solvent, preferably, dimethylformamide (DMF), is treated with an organic base such as a trialkylamine, or, preferably, triethylamine, and a trialkylsilyl halide, preferably, trimethylsilyl chloride, at a temperature of 100° C. to 160° C., preferably 140° C., to form the trialkylsilyl enol ether compound (b). Formula (c) compounds are then prepared by reacting formula (b) compounds with an alkylating agent such as a α-haloacetic acid ester such as, for example, ethyl iodoacetate in the presence of quarternary ammonium compounds, preferably, benzyl trimethylammonium fluoride, in a suitable solvent, preferably, tetrahydrofuran (THF), to provide the ester compounds (c). Ester hydrolysis with a strong base such as sodium hydroxide, potassium hydroxide, or, preferably, lithium hydroxide, in a suitable solvent such as, for example, diglyme, at a temperature of 100° C. to 175° C. yields formula (d) compounds.

Scheme II illustrates synthesis of Formula I compounds wherein there is a $C_8-C_9$ double bond (or a double bond at $C_8-C_9$ and $C_{15}-C_{16}$) and X is H. According to Scheme II, formula (c) compounds, prepared as outlined in Scheme I, are dissolved in a suitable anhydrous solvent, preferably, THF, and then treated with a base such as, for example, lithium diisopropyl amide (LDA) and an N-aryltrihaloalkylsulfonimide, preferably N-phenyltrifluoromethylsulfonimide, at a temperature of $-20°$ C. to 20° C. to yield the triflate compounds (e). Compounds (f) are prepared from compounds (e) by reaction of a solution of compounds (e) in a suitable solvent, preferably, DMF, with an organic base such as, for example, tributylamine followed by treatment with formic acid and with a phosphine ligand such as bis(diphenylphosphino)-propane, or, preferably, triphenyl phosphine, and a palladium (II) compound such as palladium (II) chloride, or preferably, palladium (II) acetate. Basic hydrolysis of compounds (f) with lithium hydroxide as described in Scheme I yields the free acid compounds (g). Formula (h) compounds are prepared from compounds (f) by selective catalytic hydrogenation of the $C_{15}-C_{16}$ double bond with a catalyst, preferably, platinum oxide, in a suitable solvent such as, for example, ethyl acetate at atmospheric pressure of hydrogen. Compounds (i) are prepared from compounds (h) by basic hydrolysis as described in Scheme I.

Scheme III outlines formation of Formula I compounds having a 3-ether or 3-ester group. According to Scheme III, the 3β-hydroxy of formula (j) is esterified with an acyl chloride such as, for example, benzoyl chloride and an aqueous hydroxide solution, such as sodium hydroxide or potassium hydroxide, held at $-10°$ C. to 0° C. to afford the ester compounds (k). Formula I compounds having a 3-alkoxy group are prepared from formula (j) compounds by etherification with an alkyl halide, preferably methyl iodide and ethyl iodide, or with a benzyl halide and a base such as, for example, potassium t-butoxide followed by aqueous alkali treatment with, preferably, lithium hydroxide in a suitable solvent, preferably, diglyme to give compounds (l).

Scheme IV depicts formation of Formula (I) compounds with or without a double bond at $C_7-C_8$, and where X is H. The starting 7-keto-$C_8-C_{14}$-ene compounds (m) are prepared from available precursors using known procedures. For example, 3β-hydroxy-7-ene compounds are treated with benzoyl chloride in pyridine to give the 3β-benzoyloxy-7-ene-compounds which are oxidized with selenium dioxide in acetic acid and then treated with chromic acid to provide 8,14-epoxide-7-keto compounds. Compounds (m) are then prepared by reduction with zinc in acetic acid. Compounds (m) are dissolved in a suitable solvent, preferably, toluene, and treated with a dialkyl aluminum cyanide reagent, preferably, diethyl aluminum cyanide, to give the 14α-carbonitriles compounds (n) after borohydride reduction of the intermediate 7-keto precursor. Compounds (o) are prepared from compounds (n) by conversion to the 7-mesylate with methanesulfonyl chloride in a base such as, for example, pyridine, followed by elimination of the mesyl group with a base, preferably, collidine at a temperature of 100° C. to 180° C. Compounds (p) are prepared from compounds (o) by reduction of the nitrile group to an aldehyde with, for example, diisobutylaluminum hydride (DiBAL), in a suitable solvent, preferably, toluene. The 14α-formyl compounds (p) are treated with a suitable Wittig reagent, preferably, (methoxymethyl)triphenylphosphonium chloride, in a solvent such as, for example, THF with sodium hydride or a lithium reagent, preferably, butyl lithium, to provide the intermediate enol ethers compounds (q) which are hydrolized by mild acid treatment to the carboxaldehyde compounds (r). Compounds (s) are prepared from compounds (r) by oxidation of the aldehyde to an acid and the hydroxy to keto group with a suitable oxidizing reagent, preferably, chromic acid in sulfuric acid, to give the intermediate compounds (s). The 3-keto group of compounds (s) are reacted with a borohydride reducing agent, preferably, sodium borohydride, in a suitable solvent such as, for example, ethanol to provide the alcohol compounds (t). Compounds (u) are prepared from compounds (t) by suitable reduction of the double bond at $C_7$-$C_8$ by catalytic hydrogenation.

Scheme V depicts the preparation of Formula (I) compounds having double bonds at $C_8$-$C_9$ and $C_{15}$-$C_{16}$. According to Scheme V, the aldehyde group in compound (aa) is reduced to the hydroxy and esterified with trifluoroacetic anhydride. The $C_8$-$C_{14}$-ene15-one group in the resulting compound is converted to a trialkylsilyl enol ether which is reacted with an α-haloacetic acid ester and a quarternary ammonium fluoride to provide the 15-keto-30-carboxylic acid ester compound (bb) by the procedure of Scheme I(a)-(b)-(c). This intermediate is treated with potassium carbonate in methanol and 4-methoxybenzyl chloride to give the p-methoxybenzyl compound (cc). This compound which has a 15-keto group is reacted according to Scheme II(c)-(e)-(f) to give the compound (dd) which has a $C_{15}$-$C_{16}$ double bond. The 4-methoxybenzyl ether is cleaved using 2,3-dichloro-5,6-dicyano-1,4-benzoquinone (DDQ) and the resulting 17hydroxyalkyl compound is converted to the 17-iodoalkyl compound which is reacted with a Grignard reagent to give compound (ff). Hydrolysis of the ester gives the acid compounds (gg).

The novel intermediates of this invention are represented by the following Formula V:

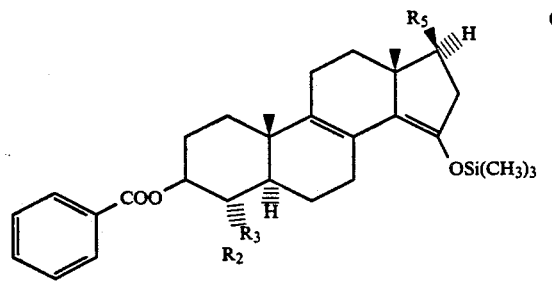

in which:

$R_2$ and $R_3$ are H, $C_1$-$C_4$alkyl or F;

$R_5$ is

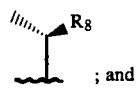

; and $R_8$ is $C_1$-$C_{11}$alkyl optionally substituted by hydroxy or carbonyl; or $C_2$-$C_{12}$alkenyl.

Formula I compounds inhibit mammalian 14α-methyl demethylase and reduce HMG-CoA reductase activity, and thus, they have therapeutic utility in treating diseases and conditions, such as hypercholesterolemia, wherein decreases in cholesterol biosynthesis produce the desired therapeutic effect.

The effectiveness of compounds of the invention to decrease HMG-CoA reductase activity in vitro is determined as follows. The activity is determined in HT29 cells, a human epithelial colon carcinoma cell line. The cells are cultured under the standard conditions of Dulbecco's minimal essential medium (DMEM), 10% fetal bovine serum, in 60 mm dishes until the cells are 50 to 70% confluent. HMG-CoA reductase activity is increased 3-5 fold, to improve the sensitivity of the experiment, by incubation for 16 hrs in DMEM medium, 5% delipidated human serum. The lipoproteins are removed from the serum by treatment with Cabosil [Weinstein, D.B. Circulation 59, Supp. II, 54 (1979)]; no cholesterol is detected by a standard cholesterol assay based on cholesterol oxidase after this treatment. After this incubation, the compounds are added as ethanol solutions to the cell culture, with no change in medium. The final ethanol concentration is 0.2% (v/v), and does not effect the enzyme activity in controls. The concentration range of the tested compounds is typically 2 nM to 2 μM, but is lower for the most potent compounds. After incubation for 6 hrs with the compounds, the cells are washed with 2×2 mL PBS, and are collected by scraping.

HMG-CoA reductase activity is determined in the crude cell extract after lysis by incubation for 10 min at 37° C. in 50 mM potassium phosphate buffer, pH 7.4, 0.2 M KCl, 5 mM EDTA, 0.25% Brij 96. The supernatant after centrifugation for 10 min at 10,000 g is assayed by the procedure reported [Edwards, P.A., Lemongello, D. Fogelman, A.M. J. Lipid Res., 20: 40–46 (1979)]. For each 60 mm dish, the protein concentration is also determined (BCA reagent, Pierce Co.), and activity is expressed as nmol mevalonate recovered/hr/mg.

The $IC_{30}$ for the effect on HMG-CoA reductase activity is estimated graphically from the plot of percent remaining activity vs. log concentration of compounds. Because many of these plots do not represent typical dose response curves in that the activity remaining plateaus at a relatively high value, an accurate estimate of $IC_{50}$ is difficult to obtain; thus the inhibitory potency of the compounds is expressed as $IC_{30}$. The $IC_{30}$ values for compounds of the invention range from about 0.8 to about 300 nanoMolar.

Mammalian 14α-methyl demethylase inhibition is determined with lanosterol 14α-demethylase purified from rat liver, or in a crude preparation of enzyme from HepG2 cells. HepG2 cells (a human hepatoma cell line) grown as for HMG-CoA reductase assays are disrupted by brief sonication. Following removal of cell debris by centrifugation, crude cell extract is used for human lanosterol 14α-demethylase assays.

Lanosterol 14α-demethylase activity is measured by use of the tritium release assay with [30-3H]-24,25 dihydrolanosterol as the substrate. [Bossard et al *J. Cell Biol.* 107:199a (1989)]. Inhibitors are initially dissolved in ethanol. Both inhibitors and substrate are diluted to the appropriate concentrations in 1 part ethanol, 1 part 2% Emulgen 913 and 8 parts 100 mM tris-Cl, 20% glycerol pH 7.5. Final ethanol and Emulgen concentrations are 1% and 0.02% respectively. Assay mix components and either purified rat liver enzyme or Hep G2 cell extract are incubated for 10 min. at 30° C. Reaction is initiated by the addition of radiolabelled substrate (37.5 μM). Rat liver enzyme assays are 15 min. and the human enzyme assays are 90 min. Ki values are determined by Dixon analysis assuming competitive inhibition. $IC_{50}$ values are determined by computer analysis of the plot of activity vs. log concentration of inhibitor. Ki values for compounds of the invention range from about 0.02 to 4.3 μM in rat liver enzyme assay.

The compounds of this invention can be tested in an in vivo test. Test compound is added to the feed in an alcoholic solution and dried. Male hamsters are fed the regulated diet feed. Blood samples are drawn 7 days before and 7 days after dosing began. Total serum cholesterol (mg/dL) is determined with a standard enzyme based kit and serum LDL plus VLDL are determined using a precipitation kit method. HDL levels are obtained by subtraction.

The pharmaceutical compositions of this invention comprise a compound of Formula I and a pharmaceutical carrier. The compounds of Formula I are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products. Standard methods for formulating pharmaceutical compositions of this type may be found in *Remington's Pharmaceutical Sciences*, Mack Publishing Company, Easton, Pa.

Doses of the compounds of Formula I in a pharmaceutical dosage unit will be an effective, nontoxic quantity selected from the range of about 0.1-100 mg/kg of active compound, preferably about 0.1-10 mg/kg. The selected dose is administered to a patient in need thereof from 1-6 times per day, orally, rectally, by injection or by infusion.

The methods of this invention to reduce HMG-CoA reductase activity in mammals, including humans, comprises administering to a subject in need of said activity an effective amount of a compounds of Formula I to produce said activity. The methods of this invention of inhibiting mammalian 14α-methyl demethylase and of reducing the biosynthesis of cholesterol and of lowering serum cholesterol levels comprise administering a compound of Formula I to a subject in need of the indicated activity in an effective amount to produce said activity.

The following examples illustrate the preparation of compounds and pharmaceutical compositions of this invention. The examples are not intended to limit the scope of the invention as defined hereinabove or as claimed below.

EXAMPLE 1

3β-Hydroxy-15-oxo-lanost-8 en-30-carboxylic acid (i)

3β-Benzoyloxy-4,4-dimethyl-15-trimethylsilyloxycholest-8,14-diene

A mixture of 3β-benzoyloxy-4,4-dimethylcholest(8(14)-en-15-one (prepared according to the technique of Knight et al., *J. Biol. Chem.*, 241:1502 (1966); mp 155°-156° C. from ethanol) (37.6 g, 0.071 mole), anhydrous dimethylformamide (DMF) (300 mL), triethylamine (58 mL, 0.42 mole) and trimethylsilyl chloride (26.6 mL, 0.21 mole) was heated under an atmosphere of argon in an oil bath held at 140° C. for 18 hours. The volatiles and DMF were evaporated in vacuo, and the residue was chromatographed over silica gel with hexane in ethyl acetate gradient to provide 3β-benzoyloxy4,4-dimethyl-15-trimethylsilyloxy-cholest-8,14-diene (38.8 g, 91%).

(ii) 3β-Benzoyloxy-15-oxo-lanost-8-en-30-carboxylic acid ethyl ester

A suspension of benzyl trimethylammonium fluoride (3.76 g, 22.2 mmole) in freshly distilled tetrahydrofuran (THF) (40 mL) was stirred with 4A molecular sieves (23 g) for 18 hours under argon. Then a solution of 3β-benzoyl-oxy-15-trimethylsilyloxy-lanost-8,14-diene (10.3 g, 17.1 mole) and ethyl iodoacetate (4.03 mL, 34.2 mmole) in THF (40 mL) was added dropwise at −10° C., the reaction was stirred an additional 15 minutes at −10° C. and 15 minutes at ambient temperature, and then diluted with hexane and filtered. Flash chromatography of the concentrated product on silica gel with a hexane in ethyl acetate gradient afforded 4.42 g 42%) of 3β-benzoyloxy-15-oxo-lanost-8-en-30-carboxylic acid ethyl ester; mp 139-142° C. - from ethanol/methanol.

(iii) 3β-Hydroxy-15-oxo-lanost-8-en-30-carboxylic acid

A solution of 3β-benzoyloxy-15-oxo-lanost-8-en-30-carboxylic acid ethyl ester (118 mg) in diglyme (5 mL) was diluted with aqueous 1N lithium hydroxide solution (5 mL) and the resulting mixture was heated at 110° C. under argon for one hour. Ethyl ether in methylene chloride (3:1) and excess 2N HCl were added and the organic layer was separated and washed with brine. The product was concentrated in vacuo by a bulb to bulb distillation to give 87 mg of solid. This was crystallized from acetonitrile to give 3β-hydroxy-15-oxo-lanost-8-en-30-carboxylic acid; mp 215°-217° C.

EXAMPLE 2

3β-Hydroxy-lanost-8.15-dien-30-carboxylic acid (i)

3β-benzoyloxy-15-trifluoromethyl-sulfonyloxy-lanost-8,15-dien-30-carboxylic acid ethyl ester A solution of 3β-benzoyloxy-15-oxo-lanost-8-en-30-carboxylic acid ethyl ester (5.36 g, 8.65 mmole) in dry THF (50 mL) was cooled to −78° C. and treated with a solution of lithium diisopropyl amide (LDA) in THF (90 mL, 14.2 mmole of LDA) and the mixture was stirred at −78° C. for one hour under argon. Then a solution of N-phenyltrifluoromethylsulfonimide (5.05 g, 14.2 mmole) in THF (20 mL) was added at −78° C., and the reaction was stirred at 0° C. for one hour. The product was partitioned between ether and brine and the dried ($MgSO_4$) solution was concentrated. Flash chromatography over silica gel with a hexane in ethyl acetate gradient provided 3β-b 1 -15-trifluoromethyl-sulfonyl-oxy-lanost-8,15-dien-30-carboxylic acid ethyl ester (5.3 g, 82%); mp 138°-139° C.

(ii) 3β-Benzoyloxy-lanost-8,15-dien-30-carboxylic acid ethyl ester

To a mixture of 3β-benzoyloxy-15-trifluoromethyl-sulfonyloxy-lanost-8,15-dien-30-carboxylic acid ethyl ester (3.48 g, 4.63 mmole), tributylamine (6.6 mL, 27.8 mmole), bis(triphenylphosphine)palladium (II) acetate (139 mg) and DMF (20 mL), held under an argon atmosphere, was added 98% formic acid (0.71 mL, 18.5 mmole), and the reaction mixture was heated at 60° C. for 5 hours. The reaction mixture was partitioned between ethyl acetate and water, the organic layer was washed with dilute HCl, brine, dilute aqueous $NaHCO_3$ solution and brine. The dried, concentrated product was chromatographed over silica gel with hexane/ethyl acetate mixtures to yield 3β-benzoyloxy-lanost-8,15-dien-30-carboxylic acid ethyl ester (1.93 g, 70%).

(iii) 3β-Hydroxy-lanost-8,15-dien-30-carboxylic acid

A mixture of 3β-benzoyloxy-lanost-8,15-dien-30-carboxylic acid ethyl ester (120 mg), diglyme (6 mL) and 1N lithium hydroxide solution (6 mL) was degassed under argon and heated at 130° C. for 4 hours. The cooled reaction mixture was partitioned between methylene chloride and dilute HCl, and the organic layer was washed repeatedly with water. The dried, concentrated extract yielded a white solid (115 mg) that was recrystallized from methanol to provide white, crystalline 3β-hydroxy-lanost-8,15-dien-30-carboxylic acid; mp 234°-236° C.

EXAMPLE 3

3β-Hydroxy-lanost-8-en-30-carboxylic acid

A mixture of 3β-benzoyloxy-lanost-8,15-dien-30-carboxylic acid ethyl ester (250 mg), ethyl acetate (30 mL) and platinum oxide (30 mg) was shaken on a Parr hydrogenation apparatus at one atmosphere of hydrogen for one hour. TLC on silica gel with 10:1 hexane/ethyl acetate indicated that the starting 8,15-diene was converted to a mixture of two products; one of the products was the reduced aromatic cyclohexane ester. This mixture was filtered, concentrated and the residue was dissolved in diglyme (4 mL) and 1N aqueous lithium hydroxide solution. The reaction mixture was heated in an oil bath held at 140° C. for 8 hours, cooled and then partitioned between ether and dilute HCl. The organic extract was washed with water, dried ($Na_2SO_4$), concentrated and the residue was crystallized from ethyl acetate/hexane to afford 3β-hydroxy-lanost-8-en-30-carboxylic acid; mp 200°-222° C.

EXAMPLE 4

14α-Carboxymethyl-3β-hydroxy-5α-cholest-8-en-15-one (i)

3β-benzoyloxy-14α-carbethoxymethyl-5α-cholest-8-en-15-one

According to the procedure described for Example 1(i), 3β-benzoyloxy-5α-cholest-8(14)-en-15-one [prepared by the procedure described in *J. Org. Chem.*, 51, 4047 (1986)] was converted to the enol ether, 3β-benzoyloxy-15-trimethylsiloxy-5α-cholest-8,14-diene, with proportional quantities of trimethylsilylchloride, triethylamine and DMF.

3β-benzoyloxy-15-trimethylsiloxy-5α-cholest-8,14-diene (1.93 g, 3.35 mmole) in THF (10 mL) and ethyl iodoacetate (0.79 mL, 6.7 mmole) was added at −10° C. to a mixture of benzyl trimethylammonium fluoride (850 mg, 5 mmole) in THF (15 mL). The mixture was stirred at −10° C. for 15 minutes and at ambient temperature for 30 minutes, diluted with hexane, filtered and the filtrate was concentrated. Using the workup described in Example 1(ii), 625 mg of 3β-benzoyloxy-14α-carbethoxymethyl-5α-cholest-8-en-15-one was obtained.

(ii)

14α-carboxymethyl-3β-hydroxy-5α-cholest-8-en-15-one

A mixture of 3β-benzoyloxy-14α-carbethoxymethyl-5α-cholest-8-en-15-one (90 mg), diglyme (5 mL) and aqueous 1N lithium hydroxide (5 ml) was heated at 125° C. under argon for 2 hours and worked up as described in the procedure for Example 1(iii). A crystallization from ethyl acetate/-hexane gave 34 mg (50%) of 14α-carboxy-methyl-3β-hydroxy-5α-cholest-8-en-15-one; mp 195°-196° C.

EXAMPLE 5

14α-Carboxymethyl-5α-cholest-8,15-dien-3β-ol (i) 3β-benzoyloxy-14α-carbethoxymethyl 15-trifluoromethylsulfonyloxy-5α-cholest-8,15-diene To a solution of lithium diisopropylamide (prepared diisopropylamine (2.1 ml, 15.3 mmole) and n-butyllithium (5.2 mL of 2.5 M, 12.9 mmole)) in THF (30 mL) held at −78° C. under argon was added a solution of 3β-benzoyloxy-14α-carbethoxymethyl-5α-cholest-8-en-15-one (4.5 g, 7.62 mmole), prepared as in Example 4(i), in THF (20 mL). After one hour at −78° C., a solution of N-phenyl-trifluoromethylsulfonimide (4.58 g, 12.9 mmole) in THF (10 mL) was added. The reaction mixture was stirred at 0° C. for an additional 2½ hours and was worked up according to the procedure described in Example 2(i) to yield 3β-benzoyloxy-14α-carbethoxymethyl-15-trifluoromethylsulfonyloxy-5α-cholest-8,15-diene (3.6 g, 65%); mp 132°-134° C.

(ii)

3β-benzoyloxy-14α-carbethoxymethyl-5α-cholest-8,15-diene

The procedure of Example 2(ii) was used. From 3β-benzoyloxy-14α-carbethoxymethyl-15-trifluoromethylsulfonyl-oxy-5α-cholest-8,15-diene (3.6 g, 5 mmole), tributylamine (8.9 mL, 37.5 mmole), bis(triphenyl-phosphine)palladium (II) acetate (150 mg), DMF (40 mL) and 98% formic acid (0.94 mL, 25 mmole) was obtained, on reaction and workup, 2.36 g (82%) of 3β-benzoyloxy-14α-carbethoxymethyl-5α-cholest-8,15-diene as a white, crystalline solid.

(iii) 14α-carboxymethyl-5α-cholest-8,15-dien-3β-ol

A mixture of 3β-benzoyloxy-14α-carbethoxymethyl-5α-cholest-8,15-diene (209 mg, 0.36 mmole) in diglyme (5 mL) and 1N lithium hydroxide (5 mL) was heated at 125° C. to 135° C. for 4 hours, and worked up according to the procedure described in Example 2(iii) to provide 122 mg (77%) of white, crystalline 14α-carboxymethyl-5α-cholest-8,15-dien-3β-ol; mp 221°-222° C. (from CH₃CN).

EXAMPLE 6

14α-Carbethoxymethyl-5α-cholest-8-en-3β-ol (i) 14α-carbethoxymethyl-5α-cholest-8-en-3β-ol A solution of 3β-benzoyloxy-14α-carbethoxymethyl-5α-cholest-8,15-diene (2.06 g, 3.58 mmole) in THF (90 mL), absolute ethanol (40 mL) and 20% ethanolic sodium ethoxide (5 mL) was heated at 75° C. for one hour. The reaction was partitioned between ethyl ether and iced dilute HCl. The organic layer was washed with water, dried and concentrated to yield the crude 14α-carbethoxymethyl-5α-cholest-8,15-dien-3β-ol. This was dissolved in ethyl acetate (150 mL) and platinum oxide (1 g) was added. The mixture was agitated under an atmosphere of hydrogen for 2 hours. The catalyst was filtered and the concentrated filtrate was flash chromatographed with 2:1 to 1:1 hexane in ethyl acetate to yield 1.59 g of 14α-carbethyoxymethyl-5α-cholest-8-en-3β-ol; mp 72°-73° C. (from CH₃CN).

(ii) 14α-carboxymethyl-5α-cholest-8-en-3β-ol

A mixture of 14α-carbethoxymethyl-5α-cholest-8-en-3β-ol (100 mg) in diglyme (3 mL) and 1N lithium hydroxide (3 mL) was heated at 130° C. for 2 hours under argon. The cooled reaction was partitioned between methylene chloride and iced dilute HCl, and the dried and concentrated organic layer provided 65 mg of 14α-carboxymethyl-5α-cholest-8-en-3β-ol; mp 191°-193° C.

EXAMPLE 7

3β-Hydroxy-lanost-8-en-30-carboxylic acid ethyl ester

3β-Benzoyloxy-lanost-8,15-dien-30-carboxylic acid ethyl ester was treated with sodium ethoxide according to the procedure described in Example 6(i) to provide 3β-hydroxy-lanost-8,15-dien-30-carboxylic acid ethyl ester. This material was catalytically reduced with hydrogen according to Example 3 to provide 3β-hydroxy-lanost-8-en-30-carboxylic acid ethyl ester mp 159°-160° C. (from petroleum ether).

EXAMPLE 8

3β-Benzoyloxy-lanost-8-en-30-carboxylic acid

The title compound is prepared from 3β-hydroxy-lanost-8-en-30-carboxylic acid (Example 3) by reaction with excess benzoyl chloride in methylene chloride with an excess of dilute aqueous sodium hydroxide at 0° C. The acidified reaction mixture is separated and the washed organic layer is dried, concentrated and chromatographed over silica gel with a hexane in ethyl acetate gradient to provide the title compound.

EXAMPLE 9

3β-Methoxy-lanost-8-en-30-carboxylic acid

A solution of 3β-hydroxy-lanost-8-en-30-carboxylic acid (100 mg) in t-butyl alcohol (5 mL) was added to a stirred solution prepared from 0.36 g of potassium metal in 20 ml of t-butyl alcohol. This reaction was stirred under argon for 10 minutes and methyl iodide (2.2 mL) was added and the mixture was stirred for 18 hours at ambient temperature. The reaction was diluted with iced dilute HCl, extracted with methylene chloride, and the dried extracts were concentrated. This product was dissolved in diglyme (3 mL) and in lithium hydroxide solution, and heated at 130° C. for 2 hours under argon. The acidified reaction mixture was extracted with methylene chloride, washed with water, and the extracts were concentrated and flash chromatographed over silica gel with a hexane in ethyl acetate gradient to afford 3β-methoxy-lanost-8-en-30-carboxylic acid.

EXAMPLE 10

3β-Hydroxy-15-oxo-lanost-8-en-30-acetic acid

The title compound is prepared according to the procedure described in Example 1(ii-iii) by using ethyl 3-iodopropionate in place of ethyl iodoacetate to afford the intermediate 3β-benzoyloxy-15-oxo-lanost-8-en-30-acetic acid ethyl ester. This ester hydrolyzed to the title compound by the procedure described in Example 1(iii).

EXAMPLE 11

3β-Hydroxy-lanost-8.15-dien-30-acetic acid

The title compound is prepared according to the procedure described in Example 2(i-iii) by using 3β-benzoyloxy-15-oxo-lanost-8-en-30-acetic acid ethyl ester (Example 10) in place of 3β-benzoyloxy-15-oxo-lanost-8-en-30-carboxylic acid ethyl ester to initially give the intermediate 3β-benzoyloxy-lanost-8,15-dien-30-acetic acid ethyl ester which is treated with a lithium hydroxide hydrolysis to provide the title compound.

EXAMPLE 12

3β-Hydroxy-lanost-8-en-30-acetic acid

The title compound is prepared according to the procedure described in Example 3 by using 3β-benzoyloxy-lanost-8,15-dien-30-acetic acid (from Example 11) in place of 3β-benzoyloxy-lanost-8,15-dien-30-carboxylic acid ethyl ester.

EXAMPLE 13

3β-benzoyloxy-lanost-7-en-30-carboxylic acid (i) 3β-benzoyloxy-4,4-dimethyl-5α-cholest-7-ene 4,4-Dimethyl-5α-cholest-7-en-3β-ol [prepared according to *J. Biol. Chem.*, 233:1343 (1958)]was converted to the title compound with benzoyl chloride in pyridine at ambient temperature for 18 hours. 3β-benzoyloxy-4,4-dimethyl-5α-cholest-7-ene had an mp of 160°-161° C. (from CH₂Cl₂/MeOH).

(ii) 3β-benzoyloxy-4,4-dimethyl-8α,14α-epoxy-5α-cholest-7-one

To a solution of 3β-benzoyloxy-4,4-dimethyl-5α-cholest-7-ene (100 g, 0.19 mole) in toluene (2.7 L) and acetic acid (2 L) was added dropwise a solution of selenium dioxide (22 g, 0.20 mole) in water (250 mL) and acetic acid (2 L). The reaction mixture was stirred for 18 hours at 25° C. Then a solution of chromium trioxide (60 g, 0.11 mole) in water (50 mL) was added dropwise After 3 hours at ambient temperature, the reaction was filtered through silica gel, diluted with a large volume of water and extracted with ether. The concentrated extracts were dissolved in methylene chloride and filtered again through silica gel. The solvent was evaporated and the residue was titrated with methanol to give 3β-benzoyloxy-4,4-dimethyl-8α,14α-epoxy-5α-cholest-7-one (60 g); mp 214°–216° C. (from CH$_2$Cl$_2$/MeOH).

(iii) 3β-benzoyloxy-4,4-dimethyl-5α-cholest-8(14)-en-7-one

A mixture of 3β-benzoyloxy-4,4-dimethyl-8α,14α-epoxy-5α-cholest-7-one (60 g, 0.11 mole), acetic acid (1 L) and zinc dust (60 g) was refluxed for 3 hours, the solids were filtered hot and the filtrate concentrated to about 150 mL. After cooling to ambient temperature, white crystals separated and were filtered and washed with cold methanol to afford 3β-benzoyloxy-4,4-dimethyl-5α-cholest-8(14)-en-7-one (40 g); mp 189°–190° C.

(iv) 3β-benzoyloxy-14α-cyano-4,4-dimethyl-5α-cholestan-7-ol

A solution of 3β-benzoyloxy-4,4-dimethyl-5α-cholest-8(14)-en-7-one (5 g, 9.4 mmole) in toluene (75 mL) at 0° C. under an argon atmosphere was treated with a solution of diethyl aluminum cyanide (1.4 M in toluene, 12.7 mL, 17 mmole). The reaction mixture was stirred at 0° C. for 0.5 hours, poured into 1N sodium hydroxide solution and extracted with methylene chloride. The organic phase was washed with water, dried and concentrated to one half the volume. An equal volume of methanol was added, the mixture was placed in a cold water bath and sodium borohydride (0.75 g) was added in portions. The mixture was stirred for 0.5 hours at ambient temperature, poured into brine, the layers separated and the organic layer was dried and concentrated to give 4.5 g (85%) of 3β-benzoyloxy-14α-cyano-4,4-dimethyl-5α-cholestan-7-ol; mp 270°–271° C. (from CH$_2$Cl$_2$).

(v) 3β-benzoyloxy-14α-cyano-4,4-dimethyl-5α-cholest-7-ene

To a solution of 3β-benzoyloxy-14α-cyano-4,4-dimethyl-5α-cholestan-7-ol (4.5 g, 8 mmole) in pyridine (100 mL) cooled to 0° C. was added methanesulfonyl chloride (2 mL). The reaction mixture was then stirred at 25° C. for 3 hours, poured into ice water, extracted with 4:1 ether/methylene chloride and washed with water The dried, concentrated mesylate was dissolved in collidine (150 mL) and refluxed for 18 hours under argon. The reaction was partitioned between iced HCl and ether/methylene chloride, and the organic extracts were washed with dilute HCl, water, aqueous sodium bicarbonate solution and brine The 6-ene impurity was removed by dissolving the product in methylene chloride, cooling to −78° C. and passing a stream of ozone through the solution until a faint blue color persists The solution was purged with argon and dimethyl sulfide was added and the solution was concentrated in vacuo. The dried, concentrated product was chromatographed over silica gel with 25/1 to 10/1 hexanes in ethyl acetate to afford 3β-benzoyloxy-14α-cyano-4,4-dimethyl-5α-cholest-7-ene (2.1 g, 48%).

(vi) 3β-hydroxy-lanost-7-en-30-al

Diisobutylaluminum hydide (1.5 M in toluene, 15 mL, 22.5 mmole) was added to a solution of 3β-benzoyloxy-14α-4,4-dimethyl-5α-cholest-7-ene (3.7 g, 6.8 mmole) in toluene held at −10° C. under argon. The reaction mixture was stirred at −10° C. for 0.5 hour, ethyl acetate (15 mL) was added slowly with cooling and the solution was then stirred at ambient temperature for 0.5 hour, treated with 1N sulfuric acid and the two phase system was refluxed for 0.5 hour. The reaction was cooled, the layers separated and the organic phase was washed with brine, dried and concentrated to the crude product. A crystallization from methylene chloride/methanol gave the white 3β-hydroxy-lanost-7-en-30-al (1.6 g, 53%); mp 123°–124° C.

(vii) 3β-Hydroxy-lanost-7-en-30-carboxaldehyde

A suspension of (methoxymethyl)triphenylphosphonium chloride (0.8 g, 2.3 mmole) in THF (5 mL) was cooled to −78° C. and n-butyl lithium 1.9 mmole) was added. The reaction turned reddish and was stirred for 15 minutes at 0° C. Then a solution of 3β-hydroxy-lanost-7-en-30-al (0.22 g, 0.47 mmole) in THF (1 mL) was added, and the mixture was stirred under argon for 15 minutes at 0° C., poured onto iced ammonium chloride solution and extracted with ether. The dried, concentrated solution was flash chromatographed over silica gel with 10/1 to 2/1 of hexane in ethyl acetate to yield 140 mg of crude Wittig product This was dissolved in acetic acid (4 mL), THF (2 mL) and water (4 mL) and heated at 70° C. for 4 hours. The reaction was diluted with water, extracted with ether and washed with water, sodium bicarbonate solution and brine The isolated crude product was chromatographed as described above for the Wittig product to provide 3β-hydroxylanost-7-en-30-carboxaldehyde (80 mg).

(viii) 3β-hydroxy-lanost-7-en-30-carboxylic acid

A solution of 3β-hydroxy-lanost-7-en-30-carboxaldehyde (75 mg) in acetone (3 mL) was cooled to 0° C. and treated with an excess of Jones reagent (chromic acid in sulfuric acid). After 15 minutes at 0° C., the reaction was quenched with isopropanol, diluted with ice and extracted well with methylene chloride The organic extracts were washed with water, stirred with sodium sulfate and concentrated. This product was dissolved in methanol (3 mL) and treated with sodium borohydride (100 mg) at 0° C. for 15 minutes. The product was partitioned between dilute HCl and ether, the organic layer was washed with brine. The dried, concentrated product was chromatographed over silica gel with a hexane in ethyl acetate gradient to give 3β-hydroxy-lanost-7-en-30-carboxylic acid (25 mg); mp 210°–212° C.

EXAMPLE 14

3β-Hydroxy-lanost-6-en-30-carboxylic acid (i) 3β-benzoyloxy-14α-cyano-4,4-dimethyl-5α-cholest-6-ene To a solution of 3β-benzoyloxy-14α-cyano-4,4-dimethyl-5α-cholestan-7-ol (100 mg, 0.18 mmole) prepared as in Example 13(iv), in dichloromethane (2.5 mL) held at −78° C. was added Martin sulfurane dehydrating agent (bis [α,α-bis(trifluoromethyl)benzenemethanolato]-diphenyl-sulfur) (240 mg, 0.36 mmole) in dichloromethane (2.5 mL). The mixture was warmed to ambient temperature, stirred for an additional 6 hours, concentrated in vacuo and the residue was triturated with methanol to give 3β-benzoyloxy-14α-cyano-4,4-dimethyl-5α-cholest-6-ene (80 mg, 82%); mp 232°–233° C. (from $CH_2Cl_2$/MeOH).

(ii) 3β-hydroxy-lanost-6-en-30-carboxylic acid

The title compound is prepared according to Example 13 (vi-viii) by using 3β-benzoyloxy-14α-cyano-4,4-dimethyl-5α-cholest-6-ene in place of 3β-benzoyloxy-14α-cyano-4,4-dimethyl-5α-cholest-7-ene.

EXAMPLE 15

3β-Hydroxy-lanostan-30-carboxylic acid

A solution of 3β-lanost-6-en-30-carboxylic acid, prepared as in Example 14, (20 mg) in ethyl acetate (5 mL) and methanol (1 mL) was treated with 10% palladium on carbon (20 mg), and the suspension was shaken on a Parr apparatus at 3 atmosphere of hydrogen. After 1 hour, the catalyst was filtered and the concentrated product was titrated with a small volume of ethyl acetate and hexane to afford the white 3β-hydroxy-lanostan-30-carboxylic acid.

EXAMPLE 16

3β-Hydroxy-14α-carboxymethyl-5α-cholest-7-ene

The title compound is prepared according to Example 13 (i-viii) by using 5α-cholest-7-en-3β-ol in place of 4,4-dimethyl-5α-cholest-7-en-3β-ol. -ol.

EXAMPLE 17

3β-Hydroxy-14α-carboxymethyl-5α-cholestane

The title compound is prepared according to Example 15 by using 3β-hydroxy-14α-carboxymethyl-5α-cholest-6-ene in place of 3β-hydroxy-5α-lanost-6-en-30-carboxylic acid.

EXAMPLE 18

3-Oxo-lanost-8,15-dien-30-carboxylic acid

A solution of 3β-hydroxy-lanost-8,15-dien-30-carboxylic acid (257 mg), prepared as in Example 2, in acetone (20 mL) was cooled in ice water and Jones reagent (1 mL) was added dropwise with stirring. The reaction was stirred an additional 10 minutes at 0° C. then quenched with 2propanol and the solvents were evaporated. The residue was partitioned between ether and brine, the ether layer was washed with brine, dried ($MgSO_4$) and concentrated to 256 mg of crude product. Chromatography on a 3mm flash column over silica gel with 5:1 to 3:1 ethyl acetate in hexane containing 1% of acetic acid gave 130 mg of product. A crystallization from acetonitrile yielded 73 mg of 3-oxo-lanost-8,15-dien-30-carboxylic acid; m.p. 212°–214° C.

EXAMPLE 19

3β-Hydroxy-15-oxo-lanost-8-en-30-propionic acid

By the procedure of Example 10 using ethyl 3-iodobutyrate, the title compound is prepared.

EXAMPLE 20

3β-Hydroxy-lanost-8-en-30-hydroxy-30-carboxylic acid

A mixture of 2.1 g of 3β-hydroxy-lanost-8-en-30-carboxylic acid ethyl ester, prepared as in Example 7, 15 ml of dichloromethane and 1.1 ml of triethylamine was cooled, using ice/methanol, under argon and 2.1 g of t-butyldimethylsilyl triflate was added dropwise. After 10 minutes, the mixture was worked up (ether/water, brine) and chromatographed eluting with 50:1 hexanes: ethyl acetate to give 3β-(t-butyldimethylsilyloxy)-lanost-8-en-30-carboxylic acid ethyl ester, mp 106°–108° C.

Lithium diisopropylamide, prepared from diisopropylamine and n-butyl lithium, in 5 ml of tetrahydrofuran was cooled to −76° C. and the above prepared ester in tetrahydrofuran was added. Then MoOPH [oxydiperoxymolybdenum(pyridine)hexamethylphosphoramide]was added and the mixture was warmed to −40° C. and stirred vigorously. The mixture was worked up to give 3β-(t-butyldimethylsilyloxy)lanost-8-en-30-hydroxy-30-carboxylic acid ethyl ester. To this ester was added 10 ml of tetrahydrofuran, 20 ml of acetonitrile and 2 ml of HFpyridine. The resulting mixture was allowed to stand for 32 hours at 20° C. The mixture was worked up and the solvent evaporated The resulting oil was chromatographed eluting with hexanes/ethyl acetate and recrystallized from methanol to give 3β-hydroxy-lanost-8-en-30-hydroxy-30-carboxylic acid ethyl ester, mp 151°–152° C.

The above prepared ester was hydrolyzed in diglyme by heating with aqueous lithium hydroxide solution at 110°–120° C. for 2.5 hours to give 3β-hydroxy-lanost-8-en-30-hydroxy-30-carboxylic acid.

EXAMPLE 21

3β-Hydroxy-lanost-8-en-30-fluoro-30-carboxylic acid

A mixture of 3β-trimethylsiloxy-lanost-8-en-30-hydroxy-30-carboxylic acid ethyl ester, prepared as in Example 20, is treated with diethylaminosulfur trifluoride in methylene dichloride to give 3β-trimethylsiloxy-lanost-8-en-30-fluoro-30-carboxylic acid ethyl ester.

This compound is treated with hydrogen fluoride pyridine followed by hydrolysis in diglyme using aqueous lithium hydroxide at 120° C. to give 3β-hydroxy-lanost-8-en-30-fluoro-30-carboxylic acid.

EXAMPLE 22

3β-Hydroxy-15-fluoro-lanost-8-en-30-carboxylic acid

3β-Benzoyloxy-15-oxo-lanost-8-en-30-carboxylic acid ethyl ester (prepared as in Example 1) in methanol is treated with sodium borohydride by the procedure of Example 13(iv) to give 3β-benzoyloxy-15-hydroxy-lanost-8-en-30-carboxylic acid ethyl ester. Treating this 15-hydroxy compound with diethylamino sulfur trifluoride in dichloromethane at −78° C. gives 3β-benzoyloxy-15-fluorolanost-8-en-30-carboxylic acid ethyl ester. This compound in diglyme is treated with aqueous lithium hydroxide by the procedure of Example 1(iii) to give 3β-hydroxy-15-fluoro-lanost-8-en-30-carboxylic acid.

EXAMPLE 23

14α-Carboxymethyl-3β-hydroxy-24(S)-methyl-5α-cholest-7,22(E)-diene (i)

3β-Benzoyloxy-24(S)-methyl-5α-cholest-8(14),22(E)-dien-7-one

A solution of 3β-benzoyloxy-24(S)-methyl-5α-cholest-7,22(E)-diene (0.19 mole) (Helv. Chim. Acta, (1975), 58, 76) was dissolved in toluene (2.7 L) and acetic acid (2L) and treated dropwise with a solution of selenium dioxide (22 g, 0.20 mole) in water (250 ml) and acetic acid (2L). The reaction mixture was stirred for 18 hours at 25° C. Then a solution of chromium trioxide (60 g, 0.11 mole) in water (50 mL) was added dropwise. After 3 hours at room temperature, the reaction was filtered through silica gel, diluted with a large volume of water and extracted with ether. The concentrated extracts were dissolved in methylene chloride and filtered through silica gel. The solvent was evaporated and the residue was triturated with methanol to give 3$\beta$-benzoyloxy-24(S)-methyl-8$\alpha$, 14$\alpha$-epoxy-5$\alpha$-cholest-22(E)-en-7-one (59 g); m.p. 149° C.–151° C.

This epoxide (59 g, 0.109 mole), acetic acid (1L) and zinc dust (60 g) were refluxed for 3 hours, the solids were filtered hot and the filtrate concentrated to about 150 mL. After cooling to ambient temperature, white crystals separated and were filtered and washed with cold methanol to provide 3$\beta$-benzoyloxy-24(S)-methyl-5$\alpha$-cholest-8(14),22(E)-dien-7-one in 43% yield; m.p. 156°–157° C.

(ii)
3$\beta$-Benzoyloxy-14$\alpha$-cyano-24(S)-methyl-5$\alpha$-cholest-22(E)-en-7-one A solution of 3$\beta$-benzoyloxy-24(E)-methyl-5$\alpha$-cholest-8(14), 22(E)-dien-7-one (3.5 g in toluene (100 mL) at 0° C. under an argon atmosphere was treated with a solution of diethyl aluminum cyanide (1.5 g, 13.5 mmole in 7.5 mL of toluene). The reaction mixture was stirred at 0° C. for 0.5 hours, poured into 1 N sodium hydroxide solution and extracted with methylene chloride. The organic phase was washed with water, dried, concentrated and flash chromatographed with 10:1 to 5:1 hexane/ethyl acetate to yield 1.3 g of 3$\beta$-benzoyloxy-14$\alpha$-cyano-24(S)-methyl-5$\alpha$-cholest-22(E)-en-7-one. A crystallization from acetone provided a white solid; m.p. 146°–148° C.

(iii)
3$\beta$-Benzoyloxy-14$\alpha$-cyano-24(S)-methyl-5$\alpha$-cholest-7,22(E)-diene A solution of 3$\beta$-benzyloxy-14$\alpha$-cyano-24(S)-methyl-5$\alpha$-cholest-22(E)-en-7-one (1.3 g in methanol (20 ml) was treated portionwise with sodium borohydride (0.4 g) at 20° C. The mixture was stirred for 0.5 hours, poured into brine, the product was extracted into 5:1 ether/methylene chloride and the organic phase was washed with brine. The dried, concentrated product was dissolved in pyridine (25 mL), cooled to 0° C. and methanesulfonyl chloride (1 mL) was added. The reaction was then stirred at 25° C. for 3 hours, poured into ice water and extracted and washed as above for the 7-hydroxy precursor. The dried, concentrated mesylate was dissolved in collidine (45 mL) and the solution was refluxed for 18 hours under argon. The reaction as partitioned between iced dilute HCl and ether/methylene chloride, and the organic extracts were washed with dilute HCl, water, aqueous sodium bicarbonate solution and brine. The dried, concentrated product was triturated with 9:1 methanol/water and the resulting solid was crystallized from methylene chloride/methanol to give 3$\beta$-benzoyloxy-14$\alpha$-cyano-24(S)-methyl-5$\alpha$-cholest-7,22(E)-diene (0.4 g); m.p. 165°–158° C.

(iv)
14$\alpha$-Carboxymethyl-3$\beta$-hydroxy-24(S)-methyl-5$\alpha$-cholest-7,22(E)-diene By the procedure of Example 13(vi), the above prepared cyano compound is reacted with diisobutylaluminum hydride in toluene to give 3$\beta$-hydroxy-14$\alpha$-formyl-24(S)-methyl-5$\alpha$-cholest-7,22(E)-diene.

By the procedure of Example 13(vii), the 14$\alpha$-formyl group is converted to the 14$\alpha$-acetaldehyde by the procedure of Example 13(viii) the aldehyde was treated with Jones reagent and sodium borohydride to give the title compound.

EXAMPLE 24

14$\alpha$-Carboxymethyl-3$\beta$-hydroxy-24-methenyl-5$\alpha$-pregn-7-ene (i)
3$\beta$-benzoyloxy-20$\beta$-carboxaldehyde-14$\alpha$cyano-5$\alpha$-pregn-7-ene A solution of 3$\beta$-benzoyloxy-14$\alpha$-cyano-24(S)-methyl-5$\alpha$-cholest-7,22(E)-diene (described in Example 23(iii) (2.5 g) was dissolved in methylene chloride (150 mL), cooled to 31 78° C. and a stream of ozone was passed through the solution until a faint blue color persisted. The solution was purged with argon and dimethyl sulfide (1 mL) was added, the solution was concentrated in vacuo and the product chromatographed with a hexane in ethyl acetate gradient to provide 3$\beta$-benzoyloxy-20$\beta$-carboxaldehyde-14$\alpha$-cyano-5$\alpha$-pregn-7-ene (1.2 g) as a white solid.

(ii) 3$\beta$-benzoyloxy-14$\alpha$-cyano-5$\alpha$-cholest-7-en-24-one

To a solution of diisopropylamine (1.7 mL, 1.2 g, 12.4 mmole) in dry THF (15 mL) cooled to −78° C. was added n-butyl lithium (4.5 mL of 2.5 M in hexane, 11.2 mmole) and the mixture was stirred under argon at −78° C. for 15 minutes. Methyl isopropylketone (1.1 mL, 0.9 g, 11.2 mmole) was added, stirring was continued for another 15 minutes and 3$\beta$-benzoyloxy-20$\beta$-carboxaldehyde-14$\alpha$-cyano-5$\alpha$-pregn-7-ene (2.6 g, 5.6 mmole) in THF (95 mL) was added at −78° C. After 5 minutes, TLC (5:1 hexane/ethyl acetate) on silica gel indicated all the starting aldehyde was consumed. The reaction mixture was poured into iced ammonium hydroxide, extracted with ether, dried and concentrated. This product was dissolved in toluene (50 mL), p-toluene sulfonic acid hydrate (300 mg) was added and the mixture was refluxed for 0.5 hours. The cooled solution was washed with water, 5% sodium bicarbonate solution and brine, and the concentrated product was triturated with methylene chloride/methanol to afford 2.1 g of 3$\beta$-benzoyloxy-14$\alpha$-cyano-5$\alpha$-cholest-7,22-dien-24-one as a white solid. This was dissolved in ethyl acetate (300 mL) and 5% palladium on carbon (200 mg) was added under argon, and the suspension was shaken on a Parr hydrogenation apparatus for 3 hours under one atmosphere of hydrogen. The suspension was filtered, the filtrate concentrated and the crude product was triturated with methanol to yield 2 g of 3$\beta$-benzoyloxy-14$\alpha$-cyano-5$\alpha$-cholest-7-en-24-one; m.p. 168°–169° C.

(iii)
14$\alpha$-Cyano-3$\beta$-hydroxy-24-methenyl-5$\alpha$-cholest-7-ene

A solution of 3$\beta$-benzoyloxy-14$\alpha$-cyano-5$\alpha$-cholest-7-en-24-one (0.25 g, 0.47 mmole) in THF (5 mL) was cooled to −78° C. under argon and trimethylsilyl methyl lithium (0.18 mmole) was added. The mixture was stirred at −78° C., the reaction was quenched by pouring into iced ammonium chloride solution and extracted with ether. The organic phase was concentrated, dissolved in THF (5 mL) and 2N HCl (10 drops) were added. After 3 hours at reflux, workup gave 0.084 g of 14α-cyano-3β-hydroxy-24-methenyl-5α-cholest-7-ene.

(iv)
14α-Carboxymethyl-3β-hydroxy-24-methenyl-5α-cholest-7-ene

By the procedures of Example 13(vi),(vii) and (viii) the above prepared 14α-cyano compound is converted to 14α-carboxymethyl-3β-hydroxy-24-methenyl-5α-cholest-7-ene.

EXAMPLE 25

3β-Hydroxy-lanost-8,15,24-trien-30-carboxylic acid (i) 3β-benzoyloxy-15-oxo-lanost-8(14),24-diene 3β-Benzoyloxy-24-hydroxy-15-oxo-lanost-8(14)ene, prepared according to the procedure of Dolle [*J. Am. Chem. Soc.*, III:278 (1989)]is treated with Martin sulfurane reagent according to the procedure of Example 14(i) to obtain the titled dehydrated product.

(ii) 3β-Hydroxy-lanost-8,15,24-triene-30-carboxylic acid

Using the procedure outlined in Example 1(i) and (ii) and Example 2(i)-(iii), 3β-benzoyloxy-15-oxo-lanost-8(14),24-diene can be converted to the titled compound.

EXAMPLE 26

An oral dosage form for administering compounds of Formula I is produced by screening, mixing and filling the ingredients into hard gelatin capsules. For example the following:

| Ingredients | Amounts |
| --- | --- |
| 3β-Hydroxy-lanost-8,15-dien-30-carboxylic acid | 50 mg |
| Magnesium stearate | 5 mg |
| Lactose | 75 mg |

EXAMPLE 27

The sucrose, calcium sulfate dihydrate and Formula I compound indicated below are mixed and granulated in the amounts shown with 10% gelatin solution. The wet granules are screened, dried, mixed with the starch, talc and stearic acid, screened and compressed into a tablet.

| Ingredients | Amounts |
| --- | --- |
| 3β-Hydroxy-14α-carboxymethyl-5α-cholest-8,15-diene | 100 mg |
| Calcium sulfate dihydrate | 150 mg |
| Sucrose | 20 mg |
| Starch | 10 mg |
| Talc | 5 mg |
| Stearic acid | 3 mg |

EXAMPLE 28

3β-Hydroxy-lanost-8-en-30-carboxylic acid (1.0 g) is dissolved in 20 g of soybean oil and emulsified by mixing with 1.2 g of egg phospholipid and enough water to bring the final volume to 100 ml. The thus formed interlipid formulation is suitable for intravenous administration.

What is claimed is:

1. A compound of the Formula I:

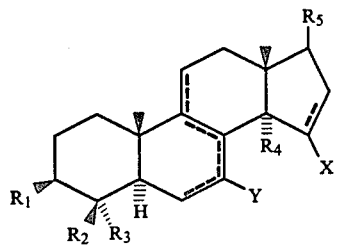

in which:
the B, C, and D rings have optional double bonds where indicated by the dotted lines, provided that the B and C rings do not have adjacent double bonds;

X and Y are H, F, OH, OR$_6$, OCOR$_7$ or keto; said X or Y being H or F when adjacent to a double bond;

R$_1$ is OH, OR$_6$, OCOR$_7$;

R$_2$ and R$_3$ are H, C$_1$-C$_4$alkyl or F;

R$_4$ is (CH$_2$)$_n$COOR$_7$, CHFCOOR$_7$ or CHOHCOOR$_7$;

R$_5$ is

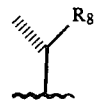

R$_6$ is C$_1$-C$_4$alkyl or benzyl;
R$_7$ is H, C$_1$-C$_6$alkyl or phenyl;
R$_8$ is C$_1$-C$_{11}$alkyl optionally substituted by hydroxy or oxo or C$_2$-C$_{11}$alkenyl; and
n is 1 to 3
and a pharmaceutically acceptable salt thereof.

2. A compound of claim 1 in which R$_5$ is:

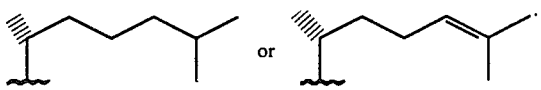

3. A compound of claim 1 in which R$_5$ is:

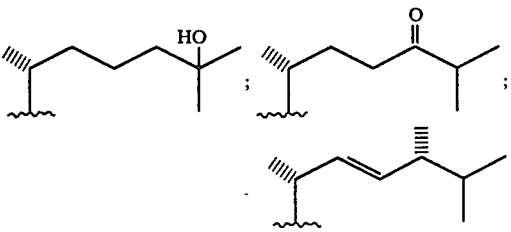

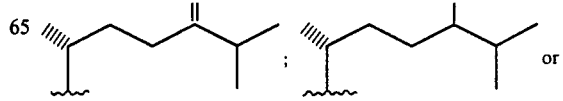

-continued

4. A compound of claim 1 having the formula:

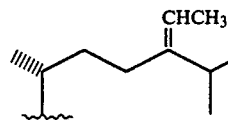

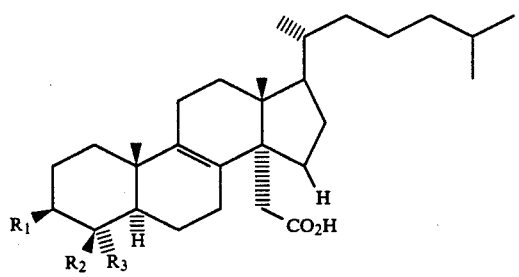

in which $R_2$ and $R_3$ are H or $CH_3$; X is H or keto and $R_1$ is as defined in claim 1.

5. A compound of claim 1 having the formula:

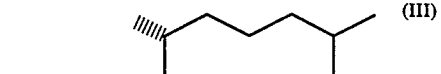

in which $R_2$ and $R_3$ are H or $CH_3$; X is H or F; and $R_1$ is as defined in claim 1.

6. A compound of claim 1 having the following formula:

in which $R_2$ and $R_3$ are H or $CH_3$; Y is H or F; and $R_1$ is as defined in claim 1.

7. A compound of claim 1 said compound being 3β-hydroxy-lanost-8,15-dien-30-carboxylic acid.

8. A compound of claim 1 said compound being 3β-hydroxy-lanost-8-en-30-carboxylic acid.

9. A compound of claim 1 said compound being 3β-hydroxy-14α-carboxymethyl-5α-cholest-8,15-diene.

10. A compound of claim 1 said compound being 3β-hydroxy-15-oxo-lanost-8-en-30-carboxylic acid.

11. A pharmaceutical composition which comprises a pharmaceutical carrier and a compound of claim 1.

12. A pharmaceutical composition of claim 11 in which the compound is 3β-hydroxy-lanost-8,15-dien-30-carboxylic acid.

* * * * *